(12) United States Patent
Devarajan

(10) Patent No.: US 7,662,578 B2
(45) Date of Patent: Feb. 16, 2010

(54) METHOD AND KIT FOR THE EARLY DETECTION OF IMPAIRED RENAL STATUS

(75) Inventor: Prasad Devarajan, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 77 days.

(21) Appl. No.: 11/737,326

(22) Filed: Apr. 19, 2007

(65) Prior Publication Data

US 2007/0248989 A1    Oct. 25, 2007

Related U.S. Application Data

(60) Provisional application No. 60/745,340, filed on Apr. 21, 2006.

(51) Int. Cl.
*G01N 33/53* (2006.01)
*G01N 33/543* (2006.01)

(52) U.S. Cl. .................. 435/7.21; 435/7.1; 436/501; 436/518; 422/61

(58) Field of Classification Search .............. 422/61
See application file for complete search history.

(56) References Cited

U.S. PATENT DOCUMENTS

| | | | |
|---|---|---|---|
| 4,444,879 A * | 4/1984 | Foster et al. | 435/7.95 |
| 2004/0219603 A1 | 11/2004 | Devarajan et al. | |
| 2005/0261191 A1 | 11/2005 | Barasch et al. | |
| 2005/0272101 A1 | 12/2005 | Devarajan et al. | |
| 2007/0037232 A1 | 2/2007 | Barasch et al. | |

OTHER PUBLICATIONS

Jain et al. (JAPI, vol. 53, Jun. 2005).*
Kumar et al. (Current Science, Vo.82, No. 6, 2002, pp. 655-663).*
Fauli et al. (Europena Journal of Anaesthestology, vol. 22, pp. 666-671).*
Fauli, A, et al., "Kidney-specific proteins in patients receiving aprotinin at high-and low-dose regimens during coronary artery bypass graft with cardiopulmonary bypass", European Journal of Anesthesiology, Jun. 2005, vol. 22, pp. 666-671.
Jain, Samta, et al., "Proteomic Analysis of Urinary Protein Markers for Accurate Prediction of Diabetic Kidney Disorder" JAPI, Jun. 2005, vol. 53, pp. 513-520.
Kumar, Yadunanda et al., "Proteomics of renal disorders: Urinary proteome analysis by two-dimensional gel electrophoresis and MALDI-TOF mass spectrometry", Current Science, Mar. 25, 2002, vol. 82, No. 6, pp. 655-663.

* cited by examiner

*Primary Examiner*—Lisa V Cook
(74) *Attorney, Agent, or Firm*—Hasse & Nesbitt LLC; Ronald J. Richter; Daniel F. Nesbitt

(57) ABSTRACT

A method and kit for identifying the presence of an early biomarker of impaired renal status following a renal event in a mammalian subject. The method typically comprises (a) providing a body fluid sample obtained from a mammalian subject following a renal event; and (b) detecting in the provided sample the presence of a protein selected from the group consisting of aprotinin, alpha-1-microglobulin (A1M), alpha-1-acid-glycoprotein (A1AG), microalbumin, and combinations thereof, the presence thereof serving as an early biomarker of a change in renal status. The method can include a kit for point-of-care detection of the early biomarker of impaired renal status. Identification of the presence or absence of the early biomarker typically directs a caregiver's therapeutic decision regarding managing treatment of the subject for impaired renal status. The invention also includes a method of assessing the administration of aprotinin during cardiopulmonary bypass surgery and provides for methods where the level of aprotinin in the subject's urine directs a caregiver's therapeutic decision regarding the intra-operative administration of aprotinin.

16 Claims, 5 Drawing Sheets

METHOD AND KIT FOR THE EARLY DETECTION OF IMPAIRED RENAL STATUS

CROSS REFERENCE TO RELATED APPLICATIONS

This application claims the benefit of U.S. Provisional Application No. 60/745,340, filed on Apr. 21, 2006.

FIELD OF THE INVENTION

The present invention relates generally to a method and kit of determining the renal status of a subject, and in particular to a method and kit of determining early impaired renal status and nephrotoxicity in a subject.

BACKGROUND OF THE INVENTION

Early detection of disease states in mammals has been the focus of much recent research. For disease detection, the public-health community has historically relied on laboratory tests that can sometimes take days or even weeks to return a result. The increased availability of better and faster diagnostic tests, however, promises the possibility of more automated and earlier disease detection and subsequent intervention. It is believed that introduction of therapy early in the disease process will reduce the mortality rate associated with the disease and shorten the time for treatment.

Acute renal failure (ARF) secondary to renal injury, including but not limited to ischemic injury and nephrotoxic injury, remains a common and potentially devastating problem in clinical nephrology. Five percent (5%) of hospital admissions and 30% of Intensive Care Unit admissions have acute renal failure, and 2-5% of hospitalized patients will develop it. Acute renal dysfunction occurs in up to 40% of adults following cardiac surgery. Pathophysiologic mechanisms include diminished renal blood flow, loss of pulsatile flow, hypothermia, atheroembolism, and a generalized inflammatory response. ARF requiring dialysis also complicates up to 10% of cardiac surgeries in infants and children with congenital heart disease.

ARF persistently continues to result in a high rate of mortality despite significant advances in supportive care. Pioneering studies over several decades have illuminated the roles of persistent vasoconstriction, tubular obstruction, cellular structural and metabolic alterations, and the inflammatory response in the pathogenesis of ARF. While these studies have paved the way for successful therapeutic approaches in animal models, translational research efforts in humans have yielded disappointing results, for reasons such as the multifaceted response of the kidney to ischemic injury and a paucity of early markers for ARF with a resultant delay in initiating therapy.

Animal studies have shown that, while ARF due to ischemia can be prevented and/or treated by several maneuvers, treatment for ARF must be instituted very early after the ischemic insult. A major reason for the inability to provide preventive and therapeutic measures for ARF in humans is the lack of early biomarkers for ARF. Thus, the identification of a reliable, early biomarker for impaired renal status would be useful to facilitate early therapeutic intervention, and help guide pharmaceutical development by providing an early indicator of nephrotoxicity.

The traditional laboratory approach for detection of renal disease involves determining the serum creatinine, blood urea nitrogen, creatinine clearance, urinary electrolytes, microscopic examination of the urine sediment, and radiological studies. These indicators are not only insensitive and nonspecific, but also do not allow for early detection of the disease. In current clinical practice, ARF is typically diagnosed by measuring a rise in serum creatinine over time, which is an unreliable indicator for measuring acute changes in kidney function. Indeed, while a rise in serum creatinine is widely considered as the "gold standard" for the detection of ARF, it is a late indicator of renal injury since as much as 50% of the kidney function may already be lost by the time the serum creatinine changes.

The lack of early biomarkers for acute renal injury thus has severely slowed progress in finding effective therapies within the narrow window of opportunity. The identification of urinary protein biomarkers suitable for the early detection and diagnosis of acute renal injury holds great promise to improve the clinical outcome of patients. It is especially important for patients presenting with vague or no symptoms or with acute renal injury following surgery such as cardiopulmonary bypass surgery.

Although efforts to evaluate disease processes and drug effects have traditionally focused on genomics, more attention has been paid recently to proteomics due to its offering a more direct, complete and promising understanding of the biological functions of a cell. The term "proteomics" was coined to make an analogy with genomics, and while it is often viewed as a continuation of genomics, proteomics is much more complicated than genomics. Most importantly, whilst the genome is a rather constant entity, the proteome differs from cell to cell and is constantly changing through its biochemical interactions with the genome and the environment. One organism will have radically different protein expression in different parts of its body, in different stages of its life cycle and in different environmental conditions.

The protein map of a biological system, including a cell, sub-cellular fraction or expression media, can be referred to as a proteome. Proteomics, or analysis of the proteome of a biological system, offers a relatively new approach to protein expression profiling and cellular or tissue protein identification from samples that are obtained under various specified conditions. Proteomics has an enormous breadth of application ranging from investigation and identification of biomarkers, molecules that are indicative of a particular pathological state, which in turn can be used for diagnostic purposes and targets for therapeutic intervention. Proteome analysis allows the investigator to obtain information on protein identity, protein-protein interaction, the level of protein expression and protein expression profiling, protein trafficking and turnover, protein variants, and protein post-translational modifications.

Traditionally, proteomics combines two-dimensional electrophoresis (2-DE), a high-resolution protein separation technique, with mass spectrometry (MS). Proteomics research is targeted towards characterization of the proteins encoded by a particular genome and its changes under the influence of biological stimulation. Proteomics also involves the study of non-genome encoded events such as the post-translation modification of proteins, interactions between proteins, and the location of proteins within the cell. The study of gene expression at the protein level is important because many of the most important cellular activities are directly regulated by proteins in the cell rather than by gene activity. Also, the protein content of a cell is highly relevant to drug discovery and drug development efforts since most drugs are designed to target proteins. Therefore, the information gained from proteomics is expected to greatly boost the number of drug targets.

Neutrophil gelatinase-associated lipocalin (NGAL) has recently been identified as an early and immediate biomarker of impaired renal status, which has been disclosed in U.S. Patent Application Publications US2004/0219603, US2005/0272101, US2005/0261191, and US2007/0037232, which are incorporated herein by reference.

Nevertheless, there remains a need to identify other reliable biomarkers for the early determination of renal injury and disease caused by ischemia and/or nephrotoxicity. It would also be advantageous to provide testing of a mammalian subject's urine, blood serum, or other body fluid samples for early biomarkers of acute renal injury within minutes or hours of a suspected injury, since early biomarkers for acute renal failure may begin to appear at low levels and continue to rise thereafter. It would likewise be advantageous if early biomarkers for acute renal injury could be detected in bodily fluid samples such as blood serum and urine shortly after the onset of a renal event that could lead to renal tubular cell injury. There is also a need to provide reliable and accurate methods of early determination of the existence of acute renal injury in patients, the results of which can then be used to manage the treatment of affected patients.

SUMMARY OF THE INVENTION

According to the methods of the present invention, four early biomarkers for predicting, diagnosing, monitoring and determining the likelihood of or extent of impaired renal status and renal tubule cell injury have been identified by standard proteomic profiling: aprotinin, alpha-1-microglobulin (A1M), alpha-1-acid-glycoprotein (A1AG), and microalbumin. Urinary aprotinin, while an early biomarker for impaired renal status, is detected only in conjunction with the intra-operative administration of aprotinin during cardiopulmonary bypass surgery.

A first aspect of the invention provides a method for determining the renal status of a mammalian subject, typically within 48 hours following a renal-injury causing event or onset of a condition that affects a change in renal status. The method comprises performing an assay on a body fluid sample obtained from a mammalian subject having, or suspected or prone to having, a renal tubular cell injury (RTCI); obtaining an assay result, wherein the assay detects in the provided sample the presence of a protein selected from the group consisting of aprotinin, alpha-1-microglobulin (A1M), alpha-1-acid-glycoprotein (A1AG), microalbumin, and combinations thereof, the presence thereof serving as an early biomarker of a change in renal status and of renal injury; and evaluating the subject's renal status based at least in part on the assay result.

A second aspect of the invention provides a method of performing an assay on a body fluid of a mammalian subject receiving intra-operative administration of aprotinin during cardiopulmonary bypass surgery and identifying the presence of urinary aprotinin therein, the method comprising the steps of: (a) providing a kit for point-of-care measurement of urinary aprotinin; (b) providing a urine sample obtained from a mammalian subject receiving intra-operative administration of aprotinin during cardio-pulmonary bypass surgery; (c) placing the sample in the kit; and (d) identifying the presence of urinary aprotinin in the sample, wherein the presence or absence of urinary aprotinin directs a caregiver's therapeutic decision regarding the intra-operative administration of aprotinin during cardiopulmonary bypass surgery.

A third aspect of the invention provides a kit for use in detection of an early biomarker of impaired renal status, the kit comprising (a) a means for acquiring a quantity of a urine sample; (b) a media having affixed thereto a capture antibody capable of complexing with an early biomarker of impaired renal status, the early biomarker selected from the group consisting of aprotinin, alpha-1-microglobulin, alpha-1-acid-glycoprotein, microalbumin, and combinations thereof; and (c) an assay for the detection of a complex of the early biomarker of impaired renal status and the capture antibody.

A fourth aspect of the invention provides a method for identifying the presence of an early biomarker of impaired renal status following a renal event in a mammalian subject, the method comprising the steps of providing a kit for point-of-care detection of an early biomarker of impaired renal status, the early biomarker selected from the group consisting of aprotinin, alpha-1-microglobulin, alpha-1-acid-glycoprotein, microalbumin, and combinations thereof. The method can also comprise the step of providing a body fluid sample obtained from a mammalian subject following a renal event or condition, typically within 48 hours and more typically well within 24 hours. The method can also comprise the step of performing an assay on the sample, including placing the sample in the kit; and identifying the presence of the early biomarker in the sample, wherein the presence or absence of the early biomarker directs a caregiver's therapeutic decision regarding managing treatment of the subject for impaired renal status. From the assay results a trained doctor can diagnose, predict, monitor, and determine the likelihood of or extent of impaired renal status and renal tubule cell injury.

A fifth aspect of the invention provides a method for monitoring the renal status of a mammalian subject being treated for impaired renal status, by performing an assay on a body fluid of the subject for identifying the presence of a urinary protein, and providing an assay result. The method comprises the steps of: (a) providing a body fluid sample obtained from a mammalian subject following a renal event; (b) identifying the presence of a protein in the sample selected from the group consisting of a 6.4 kDa protein, a 28.5 kDa protein, a 33 kDa protein, a 44 kDa protein, a 67 kDa protein and combinations thereof, the presence of the protein serving as an early biomarker of a change in renal status; (c) confirming that the protein in the sample is selected from the group consisting of aprotinin, alpha-1-microglobulin (A1M), alpha-1-acid-glycoprotein (A1AG), microalbumin, and combinations thereof, the presence thereof serving as confirmation of a change in renal status; and (d) treating for acute renal injury if the presence of one or more of the protein is confirmed.

With the methods of the present invention, the body fluid sample is typically urine, blood, serum, plasma, saliva, lymph, cerebrospinal fluid, cystic fluid, ascites, stool, bile, and any isolatable body fluid. The renal event or condition is typically diminished blood supply to the kidneys, sepsis, shock, trauma, kidney stones, kidney infection, impaired heart function, surgical procedures including cardio-pulmonary bypass surgery, admission of the subject into an intensive care unit, and the administration of medicament and potentially nephrotoxic substances, including poisons or toxins, to the subject. The medicament substances can include pharmaceuticals or iodinated contrast dyes.

The nature and advantages of the present invention will be more fully appreciated from the following drawings and detailed description.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

Figure 1:
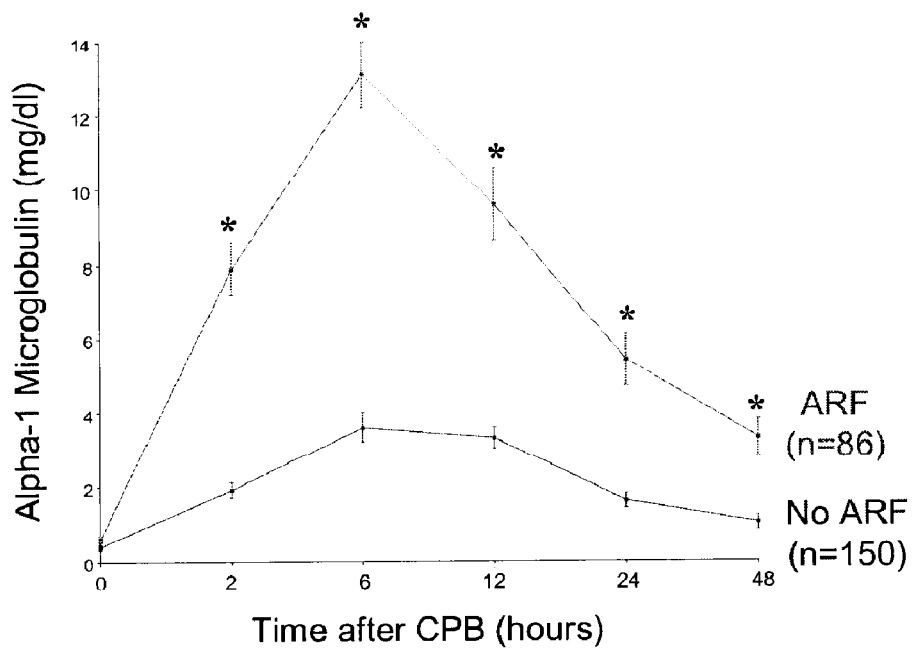
FIG. 1 is a graph showing urine alpha-1 microglobulin levels in ARF patients versus non-ARF patients at various times after cardio-pulmonary bypass, determined by quantitative nephelometry.

The practice of the present invention will employ, unless otherwise indicated, conventional methods of nephrology, molecular biology and other laboratory techniques within the skill of the art.

DEFINITIONS

In describing the invention, and as used in this specification and the appended claims, the following terms and phrases will be employed, and are intended to be defined as indicated below.

The singular forms "a," "an" and "the" include plural references unless the content clearly dictates otherwise.

The term "assay" means an analysis (e.g. via SDS PAGE, ELISA, Western Blot) done on a sample to determine the presence of a substance and/or the amount of that substance in the sample. Thus, an assay may be done, for example, to determine the level of aprotinin, A1M, A1AG, and/or albumin in a sample of a person suspected of having impaired renal status.

The term "biomarker" or "biomarkers" means a molecule or protein that is indicative of a particular pathological state. A biomarker of impaired renal status can be an ischemic renal injury biomarker (IRI biomarker), a nephrotoxic renal injury biomarker (NRI biomarker), or a mixture thereof. An effective biomarker of impaired renal status is typically a secreted protein, whereby it can be excreted by the kidney into the urine or transported within the blood serum.

The term "CPB" means cardiopulmonary bypass.

The phrase "change in renal status" means a variation or difference in an individual's renal status at one point in time as compared to another point in time.

The term "early" or "early onset" in relation to a biomarker is a biomarker protein that can appear in the blood serum or urine before the first 24 hours, more typically within the first 4-6 hours, of the onset of injury.

The term "immediate" in relation to a renal tubular cell biomarker is a biomarker protein that can appear in the blood serum within 2 hours of the onset of renal tubular cell injury.

The phrase "impaired renal status" means a decline in renal function. For example, in an individual who previously had normal kidney function but has suffered renal injury, current renal status can be classified as normal, slightly impaired, moderately impaired, and severely impaired.

The term "high amount" means an amount that is significantly higher as compared to a predetermined level.

The phrase "improved renal status" means an improvement in renal function. For example, in an individual who has received treatment for previously impaired renal status, current renal status can be classified as slightly improved, moderately improved, and greatly improved.

The term "increased amount" means an amount that is more as compared to a predetermined level.

"Managing subject treatment" refers to the behavior of the clinician or physician subsequent to the determination of the subject's renal status. As a non-limiting example, if the result of the methods of the present invention is inconclusive or there is reason that confirmation of status is necessary, the physician may order more tests. Alternatively, if the status indicates that treating for acute renal injury is appropriate, the physician may schedule the patient for the appropriate treatment. Likewise, if the status is negative (e.g., there is no indication of impaired renal status), no further action may be warranted. Furthermore, if the results show that treatment has been successful, no further management may be necessary.

The term "molecular weight" means the average molecular weight of a particular protein or biomarker that is measured, within a margin of error consistent with the measuring system being used. Experimental error and deviation should be allowed for. Unless indicated otherwise, molecular weight is molecular weight in kilodaltons (kDa).

The phrase "predetermined level" means (1) a known standard level as it pertains to levels found in samples from similar mammalian subjects which do not have a renal injury or impaired renal status; or (2) a level previously measured in a similar sample(s) from a particular mammalian subject.

The term "renal event" means an incident with a high likelihood of affecting a mammalian subject's renal function and leading to a change in renal status. As a non-limiting example, renal events can include cardio-pulmonary bypass (CPB) surgery, renal hypoperfusion, hypovolemia, hemorrhage, systemic vasodilation, low cardiac output, hyperviscosity syndrome, renovascular obstruction, infection, and allergic reactions.

The term "renal status" means the condition or state of an individual's renal function. Generally the renal status is determined to be normal, impaired or improved, as compared to predetermined levels.

The term "renal tubular cell injury" or RTCI means an injury causing impaired renal status. A RTCI can be an ischemic renal injury, a nephrotoxic renal injury, or other injury that affects the tubular cells of the kidney. RTCI can be caused by a wide variety of events that can include all varieties of diminished blood supply to the kidneys, including impaired heart function, surgical procedures that include cardiopulmonary bypass, patients in intensive care units, and the administration of pharmaceuticals, radio contrast dyes, or other medicament substances to a subject. The event can include administration or ingestion of a large and wide variety of nephrotoxins, including, but not limited to cancer chemotherapy (cisplatin, cyclophosphamide, isosfamide, methotrexate), antibiotics (gentamicin, vancomycin, tobramycin), antifungal agents (amphotericin), anti-inflammatory agents (NSAIDs), immunosuppressants (cyclosporine, tacrolimus), and radio contrast agents. The method and kit of the invention can be used to evaluate RCTI and the nephrotoxicity of both newly-developed and well-known compounds.

The term "sample" means a body fluid sample obtained from a mammalian subject. As a non-limiting example, a sample for use in the present invention can be urine, blood, serum, plasma, saliva, lymph, cerebrospinal fluid, cystic fluid, ascites, stool, bile, and any other isolatable body fluid.

The present invention provides a method and kit for the early determination of impaired renal status of a mammalian subject following a renal event or disease caused by ischemia and nephrotoxicity. The method utilizes assay methods for obtaining information on the level of protein expression, or protein expression profiling. The invention first utilized a genome-wide interrogation strategy to identify kidney genes that are induced very early after ischemia in animal models, whose protein products might serve as early biomarkers for the initiation phase of ARF. The biomarkers are first identified by distinguishing the protein profile in subjects experiencing impaired renal status or disease. Proteins in body fluid samples are defined by their mass-to-charge ratio (m/z), typically according to the SELDI-TOF-MS proteome analysis technique. This work is described in co-pending U.S. Patent Application Publications US2004/0219603, US2005/0272101, US2005/0261191, and US2007/0037232, which are incorporated herein by reference.

Using these proteomic profiling techniques, the present invention provides four distinct biomarker proteins which are predictive of impaired renal status, namely: (1) aprotinin (a 6.4 kDa protein), (2) alpha-1-microglobulin (A1M, a 28.5 kDa protein), (3) alpha-1-acid-glycoprotein (A1 AG, a 44 kDa protein), and (4) microalbumin as both a 33 kDa protein and a 67 kDa protein. The 33 kDa albumin species has been identified as a doubly protonated form of albumin, and has the same biomarker qualities of the 67 kDa species of albumin.

Although any one of these biomarker proteins is predictive of renal injury, a collection of two or more of these proteins can comprise an "ARF Panel" for the early prediction of impaired renal status. The four distinct biomarkers of impaired renal status were revealed by careful high resolution analysis using standard conditions (NP-20 chip, pH 6, 5% BSA block), that are markedly enhanced within 2 hours of cardio-pulmonary bypass (CPB) in patients who subsequently developed ARF (defined as a 50% or greater increase in serum creatinine). Standard downstream assays (ELISA or nephelometry) are available for each of these proteins, and each one is a robust biomarker.

For the aprotinin functional assay, the Unitest Aprotinin kit from Unicorn Diagnostics, Kent, UK was utilized. This is a standardized amidolytic substrate assay that measures aprotinin concentration calorimetrically. It was designed to measure aprotinin concentration in plasma. This method was adapted and modified to measure urinary aprotinin concentration. Urine is first treated with acetone to remove the effect of any serine protease inhibitors. A known amount of purified kallikrein is then added, which complexes with the aprotinin in the urine. Residual urine kallikrein activity is then measured by its ability to cleave a chromogenic peptide substrate and liberate p-nitroaniline. The concentration of p-nitroaniline is measured photometrically, and is inversely proportional to the aprotinin concentration. Reference: Gallimore M J et al. Kinins V: Advances in Experimental Medicine and Biology 247b:55-60, 1989.

Urinary A1M, A1AG and microalbumin were assayed by standard immunonephelometry (Dade Behring BN ProSpec, Deerfield, Ill.) in a CLIA-approved clinical laboratory. The intra- and inter-assay variation coefficients were <5%. A brief description of the identified proteins and results of downstream confirmatory studies are presented below.

Aprotinin. Aprotinin is a protein product produced from the lung tissue of cows and is sold under the brand name Trasylol®. Aprotinin is an approved medication that is commonly used to limit blood loss during cardiac surgery. However, a recent study has shown that the use of aprotinin is associated with a doubling in the risk of kidney failure. Aprotinin, while an early biomarker for impaired or changing renal status, is detected only in conjunction with the intra-operative administration of bovine aprotinin during cardio-pulmonary bypass surgery to control bleeding. Thus, urinary aprotinin, while an early biomarker for impaired renal status, has proven to be unique to this group, because it is detected only in conjunction with the intra-operative administration of aprotinin during cardio-pulmonary bypass surgery.

Prospective assays were performed for a 6.4 kDa protein that was suspected to be urine aprotinin in 30 patients following CPB (15 ARF and 15 controls), using proteomics. Urinary aprotinin levels (i.e. presence of a 6.4 kDa protein, detected by proteomics and later confirmed to be aprotinin by more conventional means such as SDS PAGE), at 2 hours post-CPB surgery were significantly greater (by 2.6 fold) in patients who subsequently developed ARF (2-4 days later). These results have revealed aprotinin as a highly promising candidate for the putative "ARF panel."

The rapid detection of elevated levels of aprotinin in the urine of patients, both during and immediately post-CBP surgery using proteomics, is likely the result of the administration of too high amounts of intra-operative aprotinin for that patient. Thus it may be that overzealous administration of aprotinin to control blood loss during CPB surgery can lead to impaired renal status post-operatively. The method disclosed herein of detecting aprotinin, either during or shortly post-CPB, provides an early indicator of impending impaired renal status. In addition, the presence of urinary aprotinin in patients during or post-CPB can be invaluable for therapeutic decisions regarding the intra-operative dosing of this commonly used medication.

Alpha-1-Microglobulin (A1M). A1M, also known as protein HC (for Heterogeneous Charge) is a low molecular weight 28.5 kDa glycoprotein produced primarily in the liver and kidney. It is a member of the lipocalin superfamily. Although much is now known of its structure and properties, the function and physiological role of A1M remains unclear. Very small levels of A1M are excreted in the normal urine, and a decrease in glomerular filtration results in increased levels of serum A1M. It has been suggested that A1M is also a tubular protein, and its urinary excretion is increased following tubular damage. A recent study has shown that patients with ARF who require renal replacement therapy display increased concentration of A1M in the urine early in the course of ARF.

A1M can appear in the urine within 2 hours of the onset of renal tubular cell injury. An immediate biomarker of impaired renal status can, as in the case of A1M, be present in the urine of a subject almost immediately after the onset of renal tubular cell injury. The biomarker of impaired renal status can also be an early-onset biomarker of impaired renal status that can appear within the first 24 hours, more typically within the first 6 hours, of the onset of renal tubular cell injury. As such, A1M is also an example of an early-onset biomarker of impaired renal status.

A prospective assay for urine A1M was performed on patient samples following CPB, using three independent assays: the SELDI-TOF-MS method, a standardized ELISA purchased from Immunodiagnostik, and a validated immunonephelometric test done on a Dade-Behring BN ProSpec apparatus. When compared to pre-operative levels, all three techniques reveal a consistent four to five-fold increase in urinary A1M that was detectable within 2 hours of CPB in 15 patients who subsequently developed ARF (defined as a 50% or greater increase in serum creatinine). This increase was sustained at 6 hours post CPB. Urinary A1M remained almost undetectable in 15 patients who did not develop ARF. These results have revealed A1M as one more highly promising candidate for the putative "ARF panel."

Alpha-1-Acid-Glycoprotein (A1AG). A1AG is an acute phase glycoprotein synthesized primarily in the liver. Very small levels are excreted in the normal urine. Its concentration in the serum is elevated during acute inflammatory conditions. Nothing is known about the urinary excretion of A1AG in disease states, although a recent publication has documented that exogenously administered A1AG protects against renal ischemia-reperfusion injury in animal models.

Prospectively assays for urine A1AG were performed in patients following CPB, using three independent assays— SELDI-TOF, Western blots using monoclonal antibodies purchased from Abcam (ELISA assays are not commercially available), and a validated immunonephelometric test done on a Dade-Behring BN ProSpec apparatus. When compared to baseline levels, all three techniques revealed a consistent ten to twelve-fold increase in urinary A1AG that was detectable within 2 hours post-CPB in 15 patients who subsequently developed ARF (defined as a 50% or greater increase in serum creatinine). This increase was sustained at 6 hours post CPB. Urinary A1AG remains almost undetectable in patients who do not develop ARF. These results have revealed A1AG as one more highly promising candidate for the putative "ARF panel."

Microalbumin. Microalbuminuria is an established predictor for the development of diabetic nephropathy, but can also result from acute changes in microvascular permeability, such as acute inflammation and sepsis. A recent study has shown the predictive value of microalbuminuria for the development of multi-organ failure in medical ICU patients. Prospectively assays were performed for urine microalbumin in patients following CPB, using SELDI-TOF-MS and a validated immunonephelometric test done on a Dade-Behring BN ProSpec apparatus. The results reveal a consistent five to ten-fold increase in urinary microalbumin that was detectable within 2 hours of CPB in 10 patients who subsequently developed ARF (defined as a 50% or greater increase in serum creatinine). This increase was sustained at 6 hours post CPB. When compared to baseline levels, urinary microalbumin is only slightly increased in patients who do not develop ARF. These preliminary results have also revealed microalbumin as one more promising candidate for the putative "ARF panel."

EXPERIMENTAL

The following experiments illustrate the identification of the early biomarkers of the present invention. Efforts have been made to ensure accuracy with respect to numbers used (e.g., amounts, temperatures, etc.), but some experimental error and deviation should, of course, be allowed for.

Typically Surface-Enhanced Laser Desorption/Ionization Time-of-Flight Mass Spectrometry (SELDI-TOF-MS) technology was used to initially identify the candidate biomarkers of impaired renal status of the invention, which was performed with patients undergoing open heart surgery. In particular, this technology was used with infants and children with congenital heart disease who were undergoing cardiac surgery. This population may be especially vulnerable to developing ARF since many children require multiple surgeries for step-wise repair of complex congenital anomalies. However, these children are also unique, since confounding co-morbid conditions such as advanced age, atherosclerotic vascular disease and diabetes are usually absent, rendering them an ideal patient group for examination of biomarkers as predictors of early ischemic renal injury and/or impaired renal status.

Therefore, a homogeneous population of patients with no confounding variables was studied, in whom the only conceivable renal insult would be the result of ischemia-reperfusion injury following cardio-pulmonary bypass (CPB). None of the patients studied encountered intra-operative hypotension or significant peri-operative cardiac events. To minimize intra- and post-operative volume depletion, all patients received 80-100% of their maintenance fluid requirements during and after surgery, and their hematocrits were maintained at approximately 35%.

Acute renal injury has typically been defined as a sudden decrease in renal function resulting in an inability to maintain fluid and electrolyte balance and to excrete nitrogenous wastes. Serum creatinine is a conventional biomarker. In the absence of functioning kidneys, serum creatinine concentration will increase daily by as much as 1-1.5 mg/dL. Spot urine samples were collected at baseline and at two and six hours following CPB. When the CPB time exceeded 2 hours, the first post-operative urine sample was obtained at the end of CPB, and this sample was considered as the 2-hour collection. Samples were centrifuged at 2,000 g for 5 minutes, and the supernatants stored in aliquots at −80° Celsius. Serum creatinine was measured at baseline, and routinely monitored in these critically ill children at least twice a day in the immediate post-operative period, and then at least daily beyond post-operative day three. The primary outcome variable was the development of acute renal injury, defined as a 50% or greater increase in serum creatinine from baseline. Other variables obtained included age, gender, race, bypass time, urine output, urinalysis, and urine creatinine.

Experiment 1

Equal volumes (1 µl) of urine were diluted 1:5 with sodium phosphate (pH 6) buffer, and 5 µl was spotted onto an NP20 protein array chip. Each spot was washed with distilled water, and a saturated sinapinic acid solution was used as matrix. The low intensity spectra were obtained with the laser set at an intensity of 145 and the high intensity spectra with the laser set at 195. The resulting spectra were calibrated using All-in-1 peptide/protein standards.

Experiment 2

To confirm the changes in urinary proteins observed by SELDI-TOF-MS, equal levels of samples were subjected to SDS-PAGE. Briefly, 25 µl urine samples were dissolved in an equal volume of 2×SDS-PAGE loading buffer, boiled for 10 minutes, loaded on a 10-20% Tris-Tricine gel, subjected to electrophoresis, and stained with Coomassie Blue. All values are mean±SE. SAS version 8.2 was used for statistical analysis of patient characteristics and clinical outcomes. The Mann-Whitney rank sum test was used to compare continuous variables, and Fisher's exact test was used to compare categorical variables.

Employed Method: The Biomarker Wizard (Ciphergen) was employed for initial clustering and descriptive statistics. Ciphergen Express software was used for hierarchical clustering and to generate Receiver Operating Characteristic (ROC) curves. The area under the curve was calculated to provide a measure of robustness for each biomarker. An area under the curve of 0.5 is considered no better than expected by chance, whereas a value of 1.0 signifies a perfect biomarker. Biomarker Pattern Software, an implementation of the Classification and Regression Tree algorithm, was utilized to generate predictive models for ARF based on multiple biomarkers. A 'p' value of <0.05 was considered significant.

Experiment 3

The primary outcome of acute renal injury, defined as a 50% or greater increase in serum creatinine from baseline, occurred in 15 of 60 consecutive patients, yielding an incidence rate of 25%. Out of these, 5 patients displayed an increase in serum creatinine in the 24-48 hours after CPB, but in the other 10 patients the increase was further delayed to the 48-72 hour period after CPB. Thus, the diagnosis of acute renal injury using currently accepted clinical practices could be made only days, rather than hours, after the inciting event. Based on the primary outcome, patients were classified into "control" and "ARF" (acute renal injury/failure) groups.

Comparisons were made between the ARF group (n=15) and age- and gender-matched controls (n=15). There were no significant differences between the two groups in ethnic origin, hourly urine output, urine creatinine, or urine specific gravity measurements at baseline. Patients in the ARF group encountered longer cardio-pulmonary bypass times compared with those who did not develop ARF (160±15 versus 74±9 min, p<0.05). Cardiac surgery did not result in a significant difference in urine creatinine, urine specific gravity, or hematuria in either the control or the ARF group.

patients who did not develop ARF post CPB, determined by quantitative nephelometry. The initial rise in serum creatinine was detected only after 48 hours. At all post CPB time points examined, urine A1AG was significantly greater in subjects who developed ARF, as defined by a 50% increase in serum creatinine over baseline.

Figure 3:
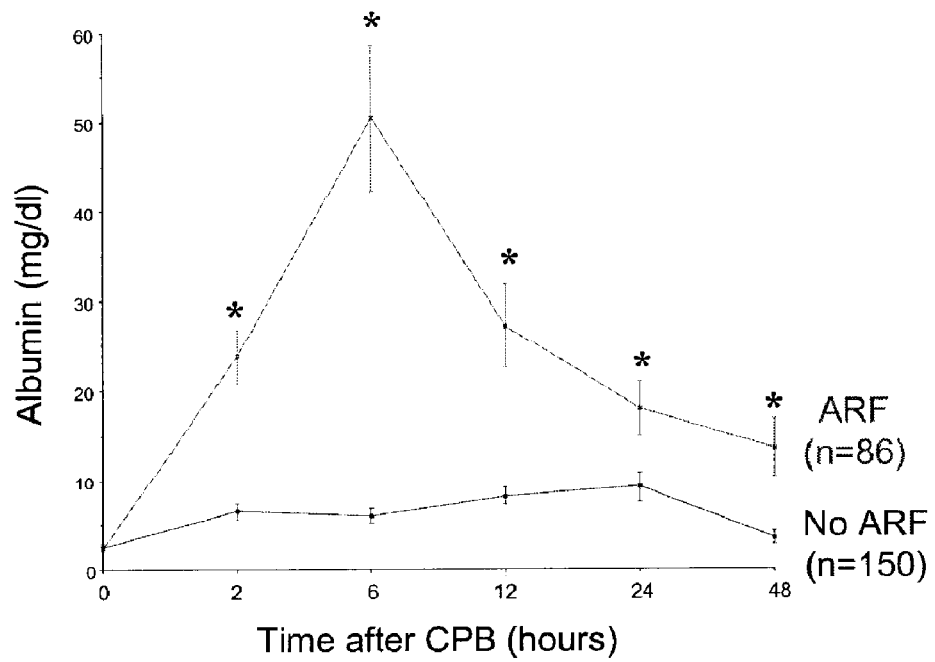
FIG. 3 is a graph showing urine microalbumin levels in ARF patients versus non-ARF patients at various times after cardio-pulmonary bypass, determined by quantitative nephelometry.

FIG. 3 shows urine microalbumin levels (in mg/dl) at 2 hrs., 6 hrs., 12 hrs., 24 hrs. and 48 hrs. after cardio-pulmonary bypass in 86 patients who subsequently developed ARF, versus 150 patients who did not develop ARF post CPB, determined by quantitative nephelometry. The initial rise in serum creatinine was detected only after 48 hours. At all post CPB time points examined, urine microalbumin was significantly greater in subjects who developed ARF, as defined by a 50% increase in serum creatinine over baseline.

Figure 4:
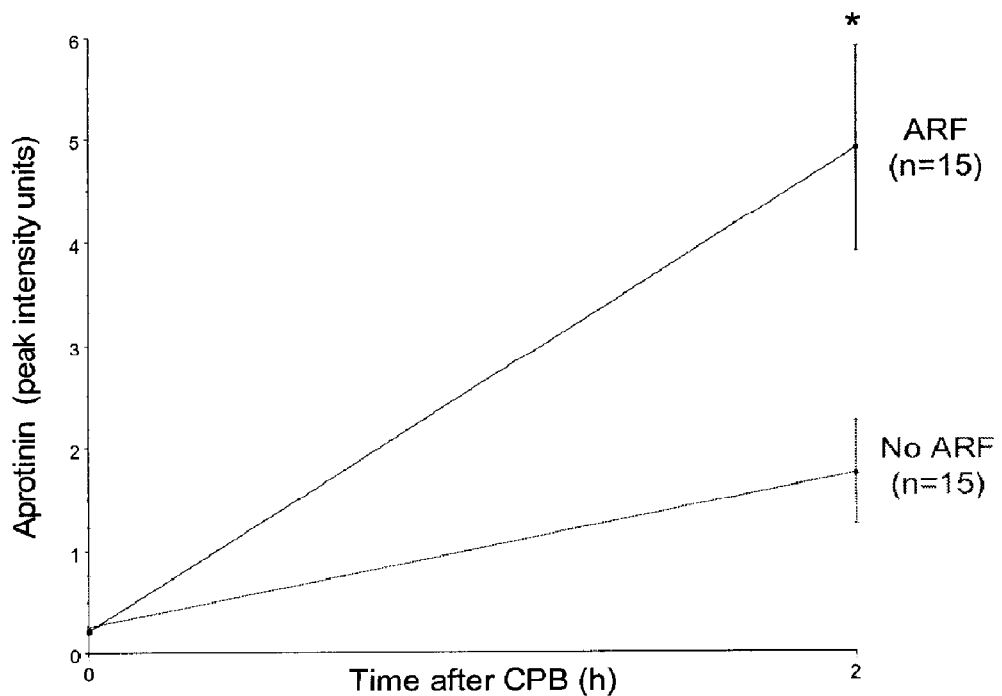
FIG. 4 is a graph showing urine aprotinin levels in ARF patients versus non-ARF patients at baseline and 2 hours after cardio-pulmonary bypass, determined by SELDI-TOF.

FIG. 4 shows urinary aprotinin levels (in peak intensity units) at baseline and 2 hours after cardio-pulmonary bypass in 15 patients who were treated with aprotinin to limit blood loss during cardiac surgery and then subsequently developed ARF, versus 15 patients who were treated with aprotinin during cardiac surgery but did not develop ARF, determined by SELDI-TOF. The initial rise in serum creatinine was detected only after 48 hours. At 2 hours post CPB, urinary aprotinin was significantly greater in subjects who developed ARF, as defined by a 50% increase in serum creatinine over baseline.

Table 1 illustrates results from a large prospective study which sought to characterize aprotinin as an early biomarker of impaired renal function. Children undergoing CPB were prospectively enrolled, and clinical data with urine samples were collected at baseline (t=0) and 2 hours (t=2).

TABLE 1

| Variable | No Aprotinin (n = 53) | With Aprotinin (n = 53) | p |
|---|---|---|---|
| Age (years) | 3.4 ± 0.6 | 5.1 ± 0.8 | Not significant |
| Boys (%) | 51 | 51 | Not significant |
| Caucasians (%) | 89 | 87 | Not significant |
| Previous surgery (%) | 13 | 72 | <0.0001 |
| Bypass time (min) | 102.5 ± 5.9 | 130.1 ± 7.8 | 0.007 |
| Aprotinin dose (KIU) | 0 | 1,127,280 ± 92,270 | <0.0001 |
| SELDI peak intensity | 0.09 ± 0.03 | 3.85 ± 0.4 | <0.0001 |
| Functional assay (KIU/ml) | 21.2 ± 3.8 | 434.2 ± 52 | <0.0001 |
| Acute Renal Injury (%) | 9.4 | 51 | <0.0001 |
| Change in creatinine (%) | 13 ± 0.1 | 71 ± 0.2 | <0.0001 |
| Days in Acute Renal Injury | 0.2 ± 0.1 | 3.0 ± 0.7 | <0.0001 |
| Days in hospital | 5.2 ± 0.5 | 14.8 ± 2.1 | <0.0001 |
| Deaths (%) | 0 | 9.4 | <0.0001 |

FIGS. 1-4 illustrate results from studies for each of the four early biomarkers of impaired renal status which are elevated following a renal event. FIG. 1 shows results from a prospective study of urinary A1M levels (in mg/dl) at various times, including 2 hrs., 6 hrs., 12 hrs., 24 hrs. and 48 hrs., after cardio-pulmonary bypass in 86 patients who subsequently developed ARF, versus 150 patients who did not develop ARF post CPB, determined by quantitative nephelometry. The initial rise in serum creatinine was detected only after 48 hours. At all post CPB time points examined, urine A1M was significantly greater in subjects who developed ARF, as defined by a 50% increase in serum creatinine over baseline.

Figure 2:
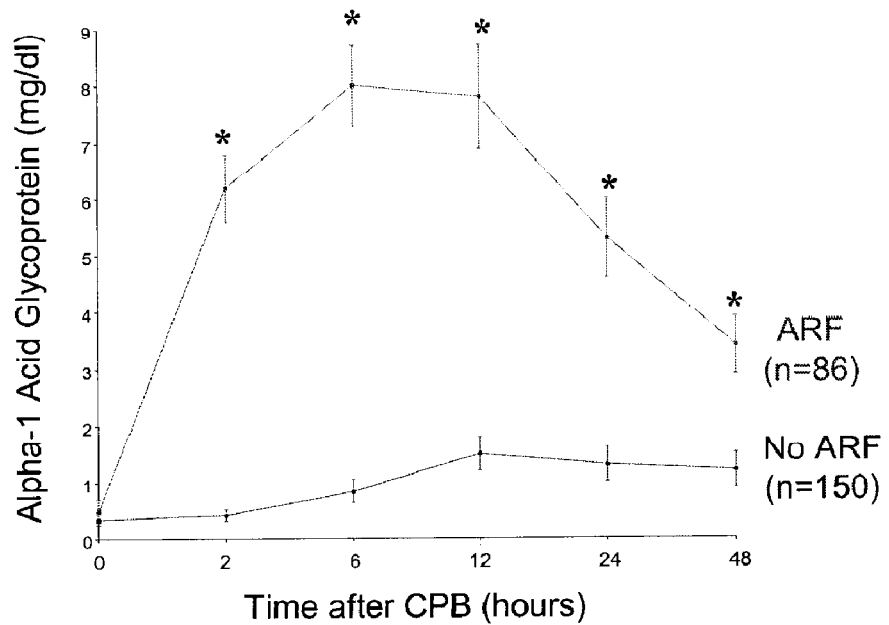
FIG. 2 is a graph showing urine alpha-1 acid glycoprotein levels in ARF patients versus non-ARF patients at various times after cardiopulmonary bypass, determined by quantitative nephelometry.

FIG. 2 shows urine A1AG levels (in mg/dl) at 2 hrs., 6 hrs., 12 hrs., 24 hrs. and 48 hrs. after cardio-pulmonary bypass in 86 patients who subsequently developed ARF, versus 150

The 6.5 kDa protein was identified as bovine aprotinin. In our prospective cohort (n=106), the incidence of acute renal injury in the 53 patients who received aprotinin was 51% versus only 9.4% in the 53 patients those who did not receive aprotinin (p<0.0001). Urinary aprotinin was measured at 2 hours post CPB by two methods. By SELDI-TOF-MS, the peak intensity of aprotinin was significantly greater in patients who developed acute renal injury (3.85±0.4 versus 0.09±0.03, p<0.0001). Similarly, functional assay performed on urine samples showed the activity of aprotinin was significantly greater in patients who developed acute renal injury (434±52 KIU/mL versus 21±4 KIU/mL, p<0.0001). Administration of aprotinin was associated with a significant increase in the duration of acute renal injury (3±0.7 versus 0.2±0.1 without aprotinin, p<0.0001), length of hospital stay (14.8A2.1 versus 5.2±0.5 without aprotinin, p<0.0001), and death (9.4% versus 0 without aprotinin, p<0.0001).

Figure 6:
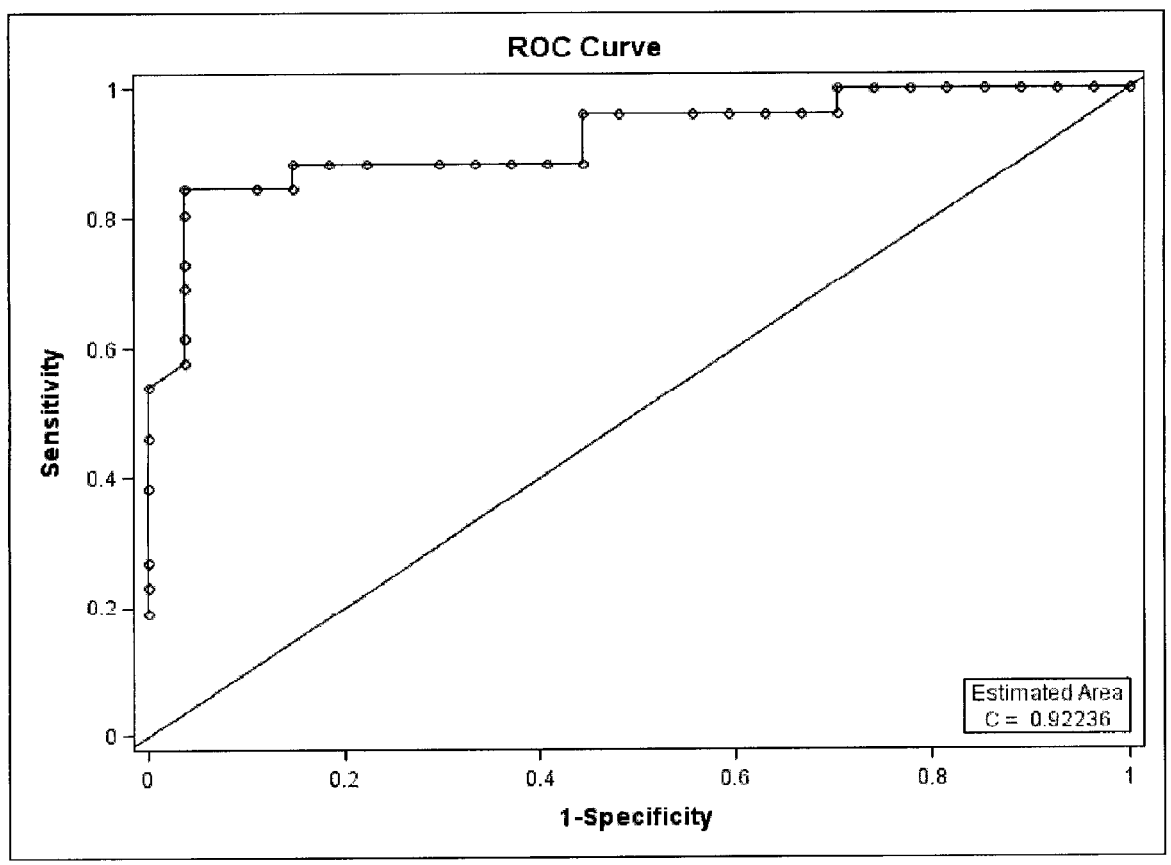
FIG. 6 is a graph showing a receiver-operating characteristic (ROC) curve for the 2 hour urinary aprotinin cutoff of 2.5 as measured by SELDI-TOF.
Figure 7:
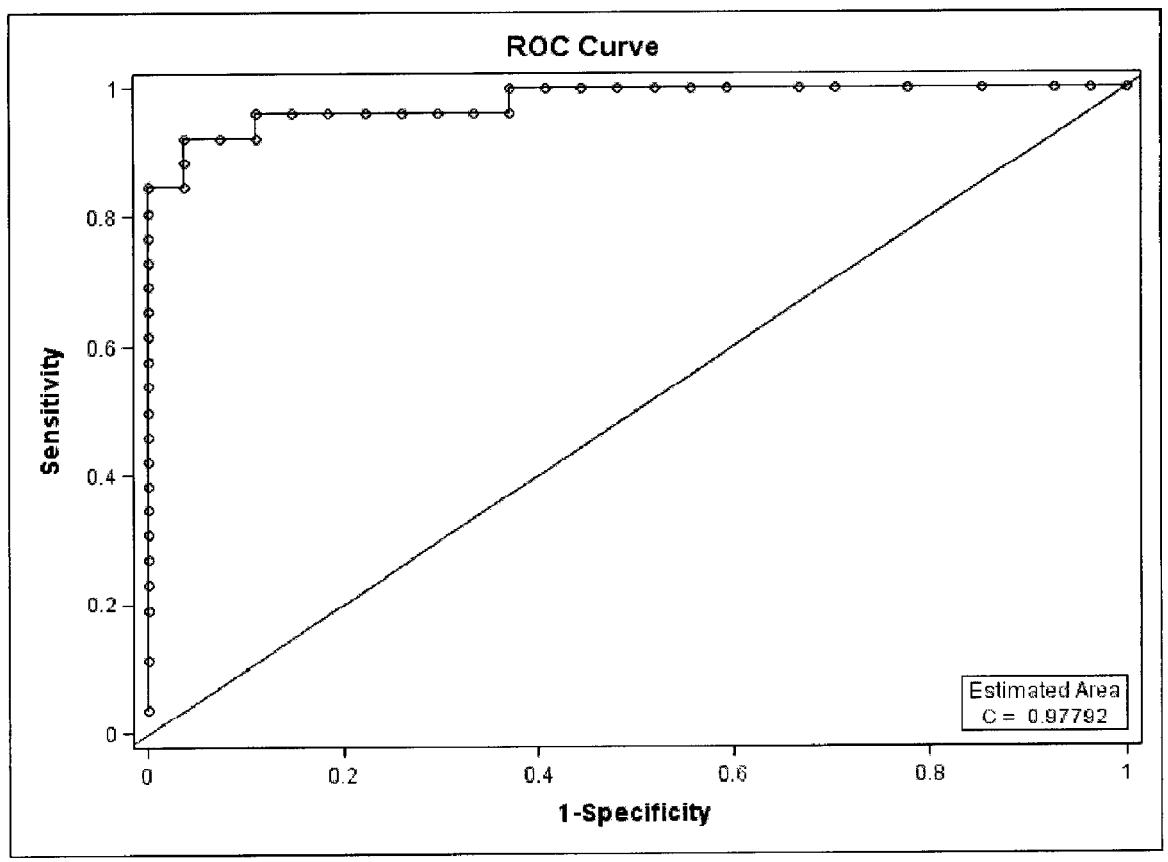
FIG. 7 is a graph showing a receiver-operating characteristic (ROC) curve for the 2 hour urinary aprotinin cutoff of 200 as measured by functional assay

Thus, urinary aprotinin measured at 2 hours post CPB is a powerful and predictive biomarker of acute renal injury. By SELDI peak intensity measurements, for a cutoff of 2.5, the sensitivity was 93%, specificity 84%, and area under the curve (AUC) was 0.92, as illustrated in Table 2 and FIG. 6. By functional assay measurements, for a cutoff of 200 KIU/ml, the sensitivity was 93%, specificity 88%, and AUC 0.98, as shown in Table 2 and FIG. 7.

TABLE 2

Aprotinin as a biomarker for the prediction of AKI

| Characteristic | Functional Assay (Cutoff 200 KIU/ml) | SELDI Peak Intensity (Cutoff 2.5) |
|---|---|---|
| Sensitivity (%) | 93 | 93 |
| Specificity (%) | 88 | 84 |
| PPV (%) | 90 | 87 |
| NPV (%) | 92 | 91 |
| AUC on ROC | 0.98 | 0.92 |

Intra-operative administration of bovine aprotinin is associated with a significant increase in incidence of acute renal injury, the severity of acute renal injury, length of hospitalization, and mortality after CPB. Urinary aprotinin measured at 2 hours post CPB is predictive of subsequent acute renal injury SDS-PAGE was applied to pooled urine samples, and the 6.5 kDa band (for aprotinin) was excised and digested with trypsin. Single MS and MS/MS spectra of peptide fragments were acquired on a tandem mass spectrometer (Applied Biosystems Q-Star XL) equipped with a PCI-1000 ProteinChip Interface. The CID spectra were submitted to Mascot (Matrix Sciences) for identification. Subsequently, SELDI-TOF-MS and a functional assay were used to quantify urinary levels of the 6.5 kDa protein.

Experiment 4

Figure 5:
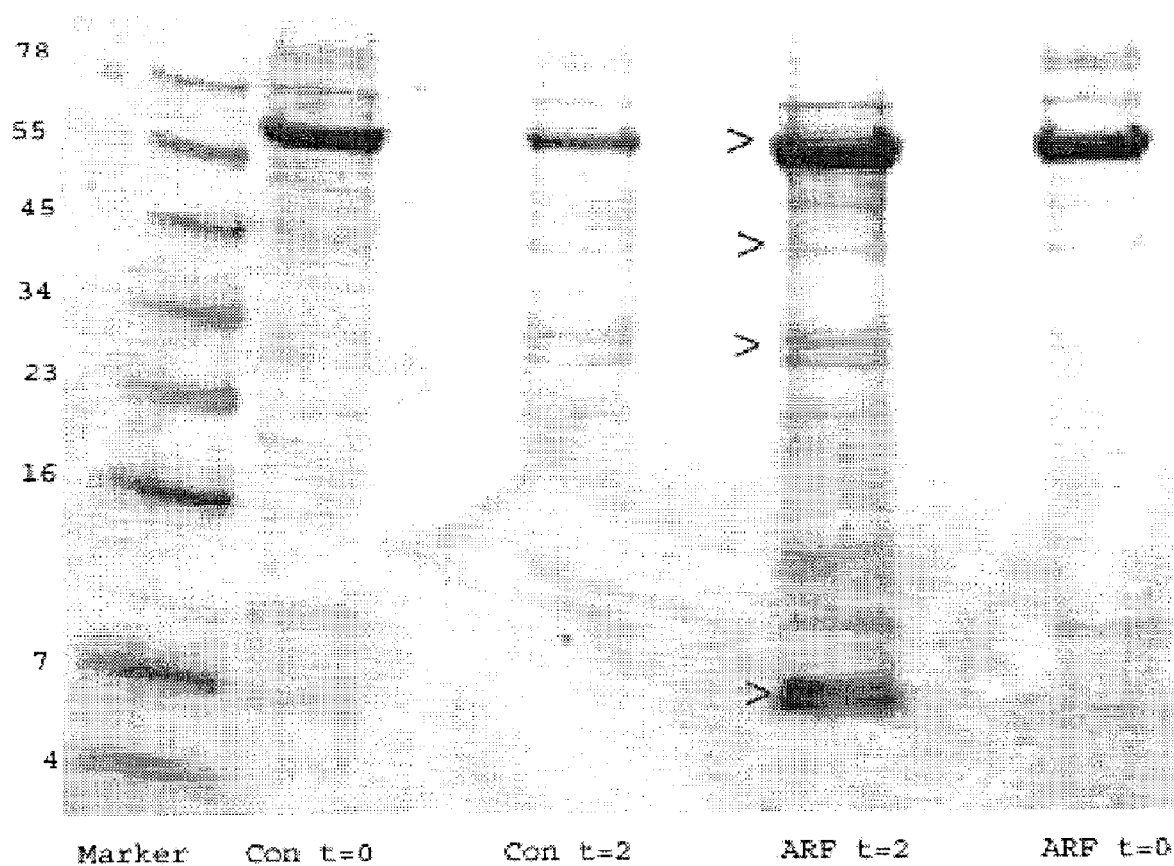
FIG. 5 is a representative gel of urine samples obtained from control and ARF patients at baseline (t=0) and 2 hours post CPB (t=2).

In order to confirm the changes in urine protein detected by SELDI-TOF-MS, samples were analyzed by gel electrophoresis and Coomassie Blue staining. A representative gel is shown in FIG. 5. Marked up-regulation of the aprotinin (6.4 kDa) and albumin (67 kDa) biomarkers was easily identified in the ARF group at 2 hours post-CPB (t=2 h), as predicted by the SELDI-TOF-MS measurements. Changes in the excretion of the A1M (28.5 kDa) and A1AG (44 kDa) biomarkers were also detectable but less apparent.

In addition to identifying the four early onset biomarkers of impaired renal status, the invention also provides a method for assessing the extent of impaired renal status based on a proportional relationship between the extent of injury, which can range from the very early onset of renal tubular cell injury, to clinical ARF, with the quantity of early biomarker proteins present in the urine, blood serum, or other isolatable body fluid of the subject. The invention provides a means for a clinician to estimate the degree of impaired renal status at an initial assessment, and to monitor the change in status of the injury over time (e.g. worsening, improving, or remaining the same). The determination of the change in status is typically based on the detected level of biomarkers of impaired renal status in the urine, blood serum, or other isolatable body fluid using known methods for obtaining information on protein identity, protein-protein interaction, the level of protein expression, or protein expression profiling.

Using the methods and techniques described herein, both a qualitative level of the biomarker of impaired renal status present in the body fluid can be analyzed and estimated, and a quantitative level of biomarker of impaired renal status present can be analyzed and measured. The clinician would select the qualitative method, the quantitative method, or both, depending upon the status of the patient. For blood samples, the quantity of blood serum to be collected is typically less than 1 milliliter (ml), and more typically less than 10 microliters (μl). A typical sample can range from about 1 μl to about 1 ml. Typically the larger quantities of a blood sample (about 1 ml) are used for quantitative assays. Typically, these small levels of blood are easily and readily available from clinical subjects who are either prone to developing ARF, or have developed ARF. Typical urine volumes are the same as typical blood volumes. These urine volumes are also typically easily available from patients with ARF.

Once an indication of impaired renal status, including renal tubular cell injury or acute renal failure, has been detected and intervention and treatment of the disease or condition has commenced, the clinician can employ the method of the invention to monitor the progress of any treatment or intervention. If a treatment or surgery that might cause renal tubular cell injury is planned, the clinician can obtain a pre-treatment sample of urine, blood serum, or other isolatable body fluid from the subject to determine a baseline biomarker value for that individual. Typically, one or more subsequent post-treatment samples will be taken and analyzed for the presence of the biomarker of impaired renal status as the treatment of the renal injury commences and continues. If a baseline value was obtained, these post-treatment values can be compared to the baseline value to determine the relative condition of the patient. The treatment can be continued until the presence of the biomarker of impaired renal status in subsequent post-treatment samples either returns to baseline value or is no longer detected. As the treatment and intervention ameliorate the condition, the expression of biomarker of impaired renal status and its presence in the subject samples will be correspondingly reduced. The degree of amelioration will be expressed by a correspondingly reduced level of biomarker of impaired renal status, such as A1M, detected in a sample. As the renal injury nears complete healing, the method can be used to detect the return to baseline levels or the complete absence of the biomarker of impaired renal status, signaling the completion of the course of treatment.

Since the biomarkers of impaired renal status disclosed herein can be easily detected within 2 hours of the renal injury or nephrotoxic treatment, the present invention, using assays for rapidly detecting and characterizing proteins present at very low levels in a body fluid sample, is suitable for use as an early-onset diagnostic. Biomarker testing of urine, blood, plasma, serum or other body fluid samples from a subject can begin within 30 minutes of a suspected injury, since biomarkers of impaired renal status begin to appear at low levels and continues to rise thereafter. Therefore, it is also of great value to initiate testing for biomarkers at any time within 2 hours of a suspected injury. Furthermore, it is of value to test at any other time during the first 24 hours following a suspected injury, since biomarkers of impaired renal status can be highly reliable and easily measured markers of injury that appear in the urine and serum before changes in other parameters, such as creatinine, can be detected. The most highly preferred course of biomarker testing is to collect samples at intervals throughout the course of treatment to monitor real time changes in renal health status.

Typically, the clinician would establish a protocol of collecting and analyzing a quantity of fresh urine and/or blood samples from the patient at selected intervals. Typically the sample is obtained intermittently during a prescribed period, and can range from a sample taken every 24 hours to a sample taken continuously. Typically the sample is taken every 6 hours, more typically every 4 hours, even more typically taken every 2 hours, and can even be taken every 30 minutes, depending on the condition of the subject. The sample can be taken and subsequently analyzed by the assay. If the sample taken is a blood sample, then a serum or plasma sample can be isolated from the blood sample by well known means.

The measurement of urinary biomarkers in patient samples provides information that diagnosticians can correlate with a probable positive diagnosis of acute renal injury or a negative diagnosis (e.g., normal or injury-free). The biomarkers are characterized by molecular weight and/or charge. The biomarkers were resolved from other proteins in a sample by using an assay for rapidly detecting and characterizing proteins present at very low levels in a body fluid sample.

Following the performing of an assay on the body fluid and obtaining an assay result for the biomarker of choice, the trained individual can contrast and compare the body fluid assay with a predetermined biomarker value, expressed in equivalent terms to the biomarker assay, to distinguish the status of the subject from some other benchmarks. For example, in one embodiment, the assay result can be compared to a first predetermined biomarker value that is predictive of the extent of renal tubule cell injury. In another embodiment, the assay result can be compared with a predetermined value that distinguishes a subject that has renal tubule cell injury from a subject that does not have a renal tubule cell injury. In yet another embodiment, the assay result can be compared with a predetermined value that predicts subsequent progression to acute renal failure, wherein an assay result that is at or greater than the predetermined value is indicative of a renal tubule cell injury that has or will subsequently develop to acute renal failure.

In still another embodiment, the assay result can be compared with a predetermined value that predicts that the renal injury will not subsequently develop to ARF, and wherein all assay result that is less than said predetermined value is indicative of a renal tubule cell injury (RTCI) that has not and will not develop to ARF. In another embodiment, the assay result can be compared to the level of the biomarker in the respective body fluid of a healthy subject who is not experiencing diminished renal function or renal injury. The selecting of the predetermined value of the respective one or more biomarkers is typically obtained by statistical analysis of a plurality of biomarker assay results, compared against the present condition and progressive condition of the subject as clinically determined by other standard renal function biomarkers.

The methods of the present invention further include managing subject treatment based on the status of the subject. The invention also provides for such methods where the biomarkers (or specific combination of biomarkers) are measured again after subject management. In these cases, the methods are used to monitor the renal status of the patient, e.g., the response to treatment. Because of the ease of use of the methods and the lack of invasiveness of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

A kit for use in the methods of the present invention typically comprises a media having affixed thereto the capture antibody, whereby the sample is contacted with the media to expose the capture antibody to the proteins contained in the sample. The kit includes an acquiring means that can comprise an implement, such as a spatula or a simple stick, having a surface comprising the media. The acquiring means can also comprise a container for accepting the sample, where the container has a sample-contacting surface that comprises the media. In an another typical embodiment, the assay for detecting the complex of the biomarker and the antibody can comprise an ELISA, and can be used to quantitate the amount of biomarker present in a sample. In an alternative embodiment, the acquiring means can comprise an implement comprising a cassette containing the media.

Early detection of the early onset biomarker of impaired renal status can provide an indication of the presence of the protein in a sample in a short period of time. Generally, a method and a kit of the present invention can detect the biomarker in a sample within four hours, more typically within two hours, and most typically within one hour, following renal tubular cell injury. Preferably, the biomarker can be detected within about 30 minutes following renal tubular cell injury.

The method and kit of the present invention for detecting the biomarker can be made by adapting the methods and kits known in the art for the rapid detection of other proteins and ligands in a biological sample. A rapid one-step method of detecting the biomarker can reduce the time for detecting the renal tubular cell injury. A typical method can comprise the steps of: obtaining a sample suspected of containing one of the four biomarkers disclosed herein; mixing a portion of the sample with a detecting antibodies for specifically binding to each of the biomarkers, so as to initiate the binding of the detecting antibodies to the biomarkers in the sample; contacting the mixture of sample and detecting antibodies with immobilized capture antibodies which specifically bind to the biomarkers, which capture antibodies do not cross-react with the detecting antibodies, so as to bind the detecting antibodies to the biomarkers, and the biomarkers to the capture antibodies, to form a detectable complex; removing unbound detecting antibodies and any unbound sample from the complex; and detecting the detecting antibodies of the complex. The detectable antibodies can be labeled with a detectable marker, such as a radioactive label, enzyme, biological dye, magnetic bead, or biotin, as is well known in the art. The detectable antibodies can be attached to a supporting material, such as a membrane, plastic strip, plastic laboratory plate such as those used for ELISA or other high-throughput assays, or any other supporting material, such as those used in other diagnostic kits well known in the art.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. A method for determining the renal status of a mammalian subject within 48 hours following a renal-injury causing event or onset of a condition that affects an acute change in renal status, the method comprising the steps of:
  a) performing an assay on a body fluid sample obtained from a mammalian subject having, or suspected or prone to having, an acute renal tubular cell injury, wherein the sample is obtained within 48 hours after said acute renal tubular cell injury;
  b) obtaining an assay result, wherein the assay detects in the sample the presence of a protein selected from the group consisting of aprotinin, alpha-1-microglobulin, alpha-1-acid-glycoprotein, microalbumin, and combinations thereof the presence thereof serving as an early biomarker of acute renal tubular cell injury; and c) evaluating the subject's renal status based at least in part on the assay result.

2. The method of claim 1, wherein the body fluid sample is selected from the group consisting of urine, blood, serum, plasma, saliva, lymph, cerebrospinal fluid, cystic fluid, ascites, stool, bile, and any other isolatable body fluid.

3. The method of claim 1, wherein the body fluid sample is urine.

4. The method of claim 1, further comprising the steps of:
d) managing subject treatment based on the determination of the subject's renal status;
e) providing a subsequent body fluid sample obtained from the subject after managing subject treatment; and
f) detecting the presence of the protein serving as the early biomarker of acute renal tubular cell injury in the subsequent sample.

5. The method of claim 4, wherein the step of managing subject treatment is selected from the group consisting of:
i) ordering more tests if the assay result is inconclusive;
ii) treating for acute renal injury if the assay detects the presence of one or more of the early biomarkers of acute renal tubular cell injury; and
iii) taking no further action if the assay does not detect the presence of one or more of the early biomarkers of acute renal tubular cell injury.

6. The method of claim 1, wherein the assay detects the presence of a plurality of early biomarkers, the plurality of biomarkers comprising alpha-1-microglobulin, alpha-1-acid-glycoprotein, and microalbumin.

7. The method of claim 1, wherein the subject has received aprotinin as a treatment to control bleeding and the early biomarker is aprotinin.

8. A method of identifying the presence of a predictive early biomarker of acute renal tubular cell injury following an acute renal-injury causing event, the method comprising the steps of:

a) performing an assay on a urine sample obtained from a mammalian subject suspected of having an acute renal tubular cell injury, wherein the sample is obtained within 48 hours following the acute renal tubular injury; and
b) obtaining an assay result, wherein the assay detects in the sample the elevated presence of a protein selected from the group consisting of alpha-1-microglobulin, alpha-1-acid-glycoprotein, and microalbumin, the presence thereof serving as a predictive early biomarker of acute renal tubular cell injury.

9. The method of claim 8, wherein the sample is obtained within 6 hours following the acute renal tubular injury.

10. The method of claim 8, wherein the sample is obtained within 2 hours following the acute renal tubular injury.

11. The method according to claim 8, wherein the assay detects the presence of a plurality of the early biomarker proteins, the plurality of biomarkers comprising alpha-1-microglobulin, alpha-1-acid-glycoprotein, and microalbumin.

12. The method according to claim 1, wherein the assay is performed by a kit for point-of-care measurement of the early biomarker protein, the kit comprising a means for acquiring a quantity of a urine sample; a media having affixed thereto a capture antibody capable of complexing with the early biomarker protein; and a detecting assay for detecting the complex of the early biomarker protein and the capture antibody.

13. The method according to claim 12, wherein the quantity of the urine sample is less than 1 ml.

14. The method according to claim 13, wherein the quantity is less than 10 microliters.

15. The method according to claim 12, wherein the acquiring means comprises an implement comprising a surface, the surface comprising the media.

16. The method according to claim 12, wherein the acquiring means comprises a container for accepting the urine sample, wherein the urine-contacting surface of the container comprises the media.

* * * * *

UNITED STATES PATENT AND TRADEMARK OFFICE
CERTIFICATE OF CORRECTION

| | |
|---|---|
| PATENT NO. | : 7,662,578 B2 |
| APPLICATION NO. | : 11/737326 |
| DATED | : February 16, 2010 |
| INVENTOR(S) | : Prasad Devarajan |

It is certified that error appears in the above-identified patent and that said Letters Patent is hereby corrected as shown below:

Column 7, line 50, delete "calorimetrically" and insert --colorimetrically--.

Column 15, line 37, delete "all" and insert --an--.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,578 B2 | Page 1 of 1 |
| APPLICATION NO. | : 11/737326 | |
| DATED | : February 16, 2010 | |
| INVENTOR(S) | : Prasad Devarajan | |

It is certified that error appears in the above-identified patent and that said Letters Patent is hereby corrected as shown below:

Please insert at column 1 after line 9, the following paragraph:

--GOVERNMENT SUPPORT

This invention was made with Government support under Grant No. R21-DK070163 awarded by the National Institutes of Health. The Government has certain rights in this invention.--

Signed and Sealed this
Tenth Day of April, 2012

David J. Kappos
*Director of the United States Patent and Trademark Office*